United States Patent [19]

Bochner

[11] Patent Number: 5,374,551
[45] Date of Patent: Dec. 20, 1994

[54] METHODS FOR DETECTION, IDENTIFICATION AND SPECIATION OF MEMBERS OF THE GENUS LISTERIA

[75] Inventor: Barry R. Bochner, Alameda, Calif.

[73] Assignee: Biolog, Inc., Hayward, Calif.

[21] Appl. No.: 920,100

[22] Filed: Jul. 24, 1992

Related U.S. Application Data

[63] Continuation-in-part of Ser. No. 549,394, Jul. 6, 1990, Pat. No. 5,134,063.

[51] Int. Cl.$^5$ .................. C12Q 1/00; C12Q 1/02
[52] U.S. Cl. ........................ 435/252.1; 435/4; 435/29; 435/34; 435/244
[58] Field of Search ............ 435/29, 34, 4, 244, 435/252.1; 436/63

[56] References Cited

U.S. PATENT DOCUMENTS

| | | | |
|---|---|---|---|
| 3,930,956 | 1/1976 | Juni | 436/6 |
| 4,016,043 | 4/1977 | Schuurs et al. | 435/5 |
| 4,018,653 | 4/1977 | Mennen | 435/295 |
| 4,038,143 | 7/1977 | Juni | 435/37 |
| 4,129,483 | 12/1978 | Bochner | 435/91.2 |
| 4,235,964 | 11/1980 | Bochner | 435/6 |
| 4,424,279 | 1/1984 | Bohn et al. | 436/534 |
| 4,683,195 | 7/1987 | Mullis et al. | 435/6 |
| 4,683,202 | 7/1987 | Mullis | 435/91.2 |
| 4,950,589 | 8/1990 | Butman et al. | 435/7.32 |
| 5,089,386 | 2/1992 | Stackebrandt et al. | 435/6 |
| 5,134,063 | 7/1992 | Bochner | 435/29 |

FOREIGN PATENT DOCUMENTS

| | | |
|---|---|---|
| 0303309 | 2/1989 | European Pat. Off. . |
| 88201530.8 | 2/1989 | European Pat. Off. . |
| 0314294 | 5/1989 | European Pat. Off. . |
| 88308820.5 | 5/1989 | European Pat. Off. . |
| PCT/EP89/-00051 | 7/1989 | WIPO . |
| 0355147 | 7/1989 | WIPO . |

OTHER PUBLICATIONS

The Shorter Bergey's Manual of Determinitive Bacteriology, Williams & Wilkins, p. 78.

J. M. Farber and P. I. Peterkin, "*Listeria monocytogenes*, a Food-borne Pathogen," Microbiol. Rev., 55:476 (1991).

J. Bille and M. P. Doyle, "Listeria and Erysipelothrix," in *Manual of Clinical Microbiology*, pp. 287–295 (A. Balows et al., eds.) (American Society for Microbiology, Washington, D.C., 1991).

B. J. Wilkinson and D. Jones, "A Numerical Taxonomic Survey of Listeria and Related Bacteria," J. Gen. Microbiol., 98:399 (1977).

J. McLauchlin, "*Listeria monocytogenes*, Recent Advances in the Taxonomy and Epidemiology of Listeriosis in Humans," J. Appl Bacteriol., 63:1 (1987).

M. L. Gray and A. H. Killinger, "*Listeria monocytogenes* and Listeric Infections," Bacteriol. Rev., 30:309 (1966).

S. A. McCarthy, "Listeria in the Environment," in Foodborne Listeriosis (A. J. Miller et al. eds.) (Society for Industrial Microbiology, Elsevier Science Publishing, Inc., New York, 1990).

J. Weis and H. P. R. Seeliger, "Incidence of *Listeria monocytogenes* in Nature," Appl. Microbiol., 30:29 (1975).

M. N. Swartz, "Other Pathogenic Microorganisms; L–Forms," in *Microbiology*, 4th edition, pp. 717–726 (B. D. Davis et al., eds) (J. B. Lippincott, Philadelphia, 1990).

R. E. Nieman and B. Lorber, "Listeriosis in Adults: A Changing Pattern. Report of Eight Cases and Review of the Literature, 1968–1978," Rev. Infect. Dis., 2:207 (1980).

B. G. Gellin et al., "The Epidemiology of Listeriosis in the United States—1986," Amer. J. Epidemiol., 133:392 (1991).

W. F. Schlech et al., "Epidemic Listeriosis—Evidence for Transmission by Food," New Eng. J. Med., 308:203 (1983).

D. W. Fleming et al., "Pasteurized Milk as a Vehicle of Infection in an Outbreak of Listeriosis," New Eng. J. Med., 312:404 (1985).

S. M. James et al., "Listeriosis Outbreak Associated with Mexican-Style Cheese—California," Morbid. Mortal. Wkly Rept. 34:357 (1985).

E. A. Szabo and P. M. Desmarchelier, "A Comparative Study of Clinical and Food Isolates of *Listeria monocytogenes* and Related Species," Epidemiol. Infect., 105:245 (1990).

H. P. R. Seeliger and D. Jones, "Genus Listeria," in *Bergey's Manual of Systematic Bacteriology*, vol. 2, pp. 1235–1245 (P. H. A. Sneath et al., eds) (Williams and Wilkins, Baltimore, 1986).

B. Skalka et al., "Routine Test for In Vitro Differentiation of Pathogenic and Apathogenic *Listeria monocytogenes* Strains," J. Clin. Micorobiol., 15:503 (1982).

V. H. Seiler and M. Busse, "Biochemische Differenzierung von Listerien aus Käse," Berl. Munch. Tierarztl. Wsch., 102:166 (1989).

Lovett et al., "A Method for Isolating *Listeria monocytogenes* From Milk," in *Abstracts of the Annual Meeting of the American Society for Microbiology*, P 17, p. 253, (American Society for Microbiology, Washington, D.C., 1985).

P. S. Hayes et al., "Isolation of *Listeria monocytogenes* from Raw Milk," Appl. Environ. Microbiol., 51:438 (1986).

R. L. Buchanan et al., "Listeria Methods Development Research at the Eastern Regional Research Center, U.S. Department of Agriculture," J. Assoc. Offic. Anal. Chem., 71:651 (1988).

J. Lovett, "Isolation and Identification of *Listeria monocytogenes* in Dairy Products," J. Assoc. Offic. Anal. Chem., 71:658 (1988).

D. McClain and W. H. Lee, "Development of USDA–FSIS Method for Isolation of *Listeria monocytogenes* from Raw Milk and Poultry,", J. Assoc. Offic. Anal. Chem., 71:660 (1988).

M. T. Knight et al., "Industry Perspectives on *Listeria monocytogenes*," J. Assoc. Offic. Anal. Chem., 71:682 (1988).

G. Comi et al., "Evaluation of an Enzymatic Method for Fast Identification of Listeria spp. in Cheese and Meat Products," Zbl. Hyg., 192:134 (1991).

A. R. Datta et al., "Synthetic Oligodeoxyribonucleotide Probes for Detection of *Listeria monocytogenes*," Appl. Environ. Microbiol., 54:2933 (1988).

J. Klinger, "Comparative Studies of Nucleic Acid Hybridization for Listeria in Foods," J. Assoc. Offic. Anal. Chem., 71:669 (1988).

G. R. Siragusa and M. G. Johnson, "Monoclonal Antibody Specific for *Listeria monocytogenes, Listeria innocua,* and *Listeria welshimeri*," Appl. Environ. Microbiol., 56:1897 (1990).

J. A. Mattingly, "Rapid Monoclonal Antibody-Based Enzyme-Linked Immunosorbent Assay for Detection of Listeria in Food Products," J. Assoc. Offic. Anal. Chem., 71:679 (1988).

A. P. MacGowan et al., "Evaluation of API 20 STREP System for Identifying Listeria Species," J. Clin. Pathol. 42:548 (1989).

K. G. Kerr et al, "Evaluation of the Mast ID and API 50CH Systems for Identification of Listeria spp.," Appl. Environ. Microbiol., 56–657 (1990).

B. Bochner and M. Savageau, "Generalized Indicator Plate for Genetic, Metabolic and Taxonomic Studies with Microorganisms," Appl. Environ. Microbiol., 33:434 (1977).

M. J. Loessner et al., "Comparison of Seven Plating Media for Enumeration of Listeria spp.," Appl. Environ. Microbiol., 54:3003 (1988).

R. L. Buchanan et al., "Comparison of Lithium Chloride-Phenylethanol-Moxalactam and Modified Vogel-Johnson Agars for Detection of Listeria spp. in Retail-Level Meats, Poultry, and Seafood," Appl. Environ. Microbiol., 55:599 (1989).

R. V. Lachica, "Selective Plating Medium for Quantitative Recovery of Food–Borne *Listeria monocytogenes*," Appl. Environ. Microbiol., 56:167 (1990).

A. Janik et al., "Genetic Transformation as a Tool for Detection of *Neisseria gonorrhoeae*," J. Clin. Microbiol., 4:71 (1976).

R. D. Lucas and R. E. Levin, "Genetic Transformation Between Strains of *Listeria monocytogenes*," Lett. Appl. Microbiol., 9:215 (1989).

Sambrook et al., (eds.), "Identification of Recombinant Clones," *Molecular Cloning: A Laboratory Manual*, 2d edition, (Cold Spring Harbor Laboratory, Cold Spring Harbor, N.Y., 1989).

J. Douillard and T. Hoffman, "Basic Facts About Lymphocyte Hybridomas," in *Compendium of Immunology*, vol. II (L. M. Schwartz, ed.) (Van Nostrand Reinhold, 1981).

G. Kohler and C. Milstein, "Continuous Cultures of Fused Cells Secreting Antibody of Predefined Specificity," Nature 256:495 (1975).

G. Kohler and C. Milstein, "Derivation of Specific Antibody-Producing Tissue Culture and Tumor Lines by Cell Fusion," Eur. J. Immunol., 6:511 (1976).

C. L. Reading, "Theory and Methods for Immunization in Culture and Monoclonal Antibody Production," J. Immunol. Meth., 53:261 (1982).

F. Mat-Jan et al., "Mutants of *Escherichia coli* Deficient in the Fermentative Lactate Dehydrogenase," J. Bacteriol., 171:342 (1989).

E. Pradel et al., "Nucleotide Sequence and Transcriptional Analysis of the *Escherichia coli agp* Gene Encoding Periplasmic Acid Glucose-1-Phosphate," J. Bacteriol., 172:802 (1990).

M. Futai and H. Kimura, "Inducible Membrane-Bound L-Lactate Dehydrogenase From *Escherichia coli*," J. Biol. Chem., 252:5820 (1977).

B. E. Britigan et al., "Phagocyte-Derived Lactate Stimulates Oxygen Consumption by *Neisseria gonorrhoeae*," J. Clin. Invest., 81:318 (1988).

D. J. Hassett and M. S. Cohen, "Bacterial Adaptation to Oxidative Stress: Implications for Pathogenesis and Interaction with Phagocytic Cells," FASEB J., 3:2574 (1989).

H. Smith, "Pathogenicity and the Microbe in vivo," J. Gen. Microbiol., 136:377 (1990).

A. Schuchat et al., "Role of Foods in Sporadic Listeriosis. I. Case-Control Study of Dietary Risk Factors," J. Amer. Med. Assoc., 267:2041 (1992).

R. W. Pinner et al., "Role of Foods in Sporadic Listeriosis. II. Microbiologic and Epidemiologic Investigation," J. Amer. Med. Assoc., 267:2046 (1992).

M. J. Linnan et al., "Epidemic Listeriosis Associated with Mexican-Style Cheese," New Eng. J. Med., 319:823 (1988).

W. F. Schlech, "Expanding the Horizons of Foodborne Listeriosis," J. Amer. Med. Assoc., 267:2081 (1992).

J. Roucourt and R. A. D. Grimont, "*Listeria welshimeri* sp. nov. and *Listeria seeligeri* sp. nov." Internat. J. System. Bacteriol., 33:866 (1983).

R. V. Lachica, "Same-Day Identification Scheme for Colonies of *Listeria monocytogenes*," Appl. Environ. Microbiol., 56:1166 (1990).

J. Freney et al., "Evaluation of API Coryne in Comparison with Conventional Methods for Identifying Coryneform Bacteria," J. Clin. Microbiol., 29:38 (1991).

E. Merck, Frankfurter Strasse 250, D-6100 Darmstadt, Federal Republic of Germany, Bactident ® Aminopeptidase Product Information (1991).

S. E. Gavin et al., "Evaluation of the Rapid CORYNE Identification System for Corynebacterium Species and Other Coryneforms," J. Clin. Microbiol., 30:1692 (1992).

E. Bannerman et al., "Evaluation of the Organon-Teknika MICRO-ID Listeria System," Appl. Environ. Microbiol., 58:2011 (1992).

J. Bille et al., "API Listeria, a New and Promising One-Day System to Identify Listeria Isolates" Appl. Environ. Microbiol., 58:1857 (1992).

I. Caniaux et al., "API Listeria, a New Identification System for Listeria" Abstracts of the American Society for Microbiology 92nd General Meeting, 26–30 May, 1992, C9, p. 422 (American Society for Microbiology, Washington, D.C., 1992).

P. Kämpfer et al., "Physiological Characterization and Identification of Listeria Species," Zbl. Bakt, 275:423 (1991).

P. Kämpfer, "Differentiation of Corynebacterium spp., Listeria spp., and Related Organisms by Using Fluorogenic Substrates," J. Clin. Microbiol., 30:1067 (1992).

K. G. Kerr and R. W. Lacey, "Isolation and Identification of *Listeria monocytogenes*," J. Clin. Pathol., 44:624 (1991).

J. D. Klinger, "Isolation of Listeria: A Review of Procedures and Future Prospects," Infection 16(Suppl. 2): S98 (1988).

N. C. Klein et al., "Listeria," Infect. Control Hosp. Epidemiol., 12:311 (1991).

J. Rocourt et al., "Différenciation Biochimique des Groupes Génomiques de *Listeria monocytogenes* (Sensu Lato)" Ann. Microbiol. (Inst. Pasteur) 134A:65 (1983).

J. Rocourt et al., "DNA Relatedness Among Serovars of *Listeria monocytogenes* sensu lato," Current Microbiol., 7:383 (1982).

M. D. Collins et al., "Phylogenetic Analysis of the Genus Listeria Based on Reverse Transcriptase Sequencing of 16S rRNA," Internat. J. System. Bacteriol., 41:240 (1991).

P. Boerlin et al., "Listeria ivanovii subsp. Iondoniensis subsp. nov.," Internat. J. System. Bacteriol., 42:69 (1992).

C. Jacquet et al., "Use of rRNA Gene Restriction Patterns for the Identification of Listeria Species," System. Appl. Bacteriol., 15:42 (1992).

J. Rocourt et al., "Assignment of *Listeria grayi* and *Listeria murrayi* to a Single Species, *Listeria grayi*, with a Revised Description of *Listeria grayi*," Internat. J. System. Bacteriol., 42:171 (1992).

P. Boerlin et al., "Taxonomy of the Genus Listeria by Using Multilocus Enzyme Electrophoresis," Internat. J. System. Bacteriol., 41:59 (1991).

M. Tabouret et al., "Analysis of Surface Proteins of Listeria in Relation to Species, Serovar and Pathogenicity," J. Gen. Microbiol., 138:743 (1992).

B. Ninet et al., "Quantitative Analysis of Cellular Fatty Acids (CFAs) Composition of the Seven Species of Listeria," System. Appl. Microbiol., 15:76 (1992).

*Primary Examiner*—Michael G. Wityshyn
*Assistant Examiner*—Jane A. Williams

*Attorney, Agent, or Firm*—Haverstock, Medlen & Carroll

[57] ABSTRACT

The present invention relates generally to differential carbon source metabolism in the genus Listeria, metabolic, biochemical, immunological and genetic procedures to measure said differential carbon source metabolism and the use of these products to detect, isolate and/or distinguish species of the genus Listeria as well as detect, isolate and/or distinguish strains of species of Listeria. The present invention also contemplates test kits and enrichment media to facilitate these procedures.

6 Claims, No Drawings

METHODS FOR DETECTION, IDENTIFICATION AND SPECIATION OF MEMBERS OF THE GENUS LISTERIA

This invention is a continuation-in-part of U.S. patent application Ser. No. 07/549,394, filed 6 Jul. 1990, now U.S. Pat. No. 5,134,063. The invention described herein was made in the course of or under grants from the United States Government.

FIELD OF THE INVENTION

The present invention relates to differential metabolism as a basis for detection and identification of members of the genus Listeria.

BACKGROUND OF THE INVENTION

Introduction to Listeria and Taxonomy. Bacteria belonging to the genus Listeria are Gram-positive, nonspore forming, motile rods characterized in part by their capability for growth over a wide range of temperatures ($-0.4°$ C. to 45° C.) (J. M. Farber and P. I. Peterkin, Microbiol. Rev., 55:476 (1991)) and pH ($\leq 5.5$ to 9.5) (J. Bille and M. P. Doyle, in Manual of Clinical Microbiology, pp. 287-295 (A. Balows et al., eds) (American Society for Microbiology, Washington, D.C., 1991)).

The taxonomic relationships between the genus and allied Gram-positive taxa are not clear. Listeria were previously included within the family Corynebacteriaceae, but are now taxonomically included in the Clostridium-Lactobacillus-Bacillus branch of the gram-positive bacteria phylogeny. Table 1 contains a list of Listeria species. One organism, previously named L. denitrificans, has been reclassified into a new genus, Jonesia. The new name of this organism is J. denitrificans; this organism is not included in the table.

TABLE 1
SPECIES OF THE GENUS LISTERIA

L. grayi
L. innocua
L. ivanovii subspecies ivanovii
L. ivanovii subspecies londoniensis
L. monocytogenes
L. murrayi*
L. seeligeri
L. welshimeri

*Some researchers include L. murrayi within L. grayi.

Because all Listeria isolates show a high degree of DNA relatedness and very close similarity in biochemical, phenotypic and protein characteristics, there is disagreement in the field regarding relationships between the identified species within the genus. B. J. Wilkinson and D. Jones, J. Gen. Microbiol., 98:399 (1977). J. McLauchlin, J. Appl. Bacteriol., 63:1 (1987).

Although there are disagreements between taxonomists, there remains the necessity of identifying members of the Listeria genus to the species level, in order to facilitate assessment of an isolate's pathogenic potential for humans as well as other animals. L. monocytogenes is a well-documented opportunistic pathogen of humans and other animals. L. ivanovii is most commonly pathogenic for animals other than humans, while L. grayi, L. innocua, L. murrayi and L. welshimeri are generally considered nonpathogenic. Thus, if the isolate from silage is identified as L. monocytogenes, it is a significant cause for concern to people such as ranchers and dairy farmers. If on the other hand, the isolate is L. murrayi, it is much less significant.

Natural History

Listeria species are ubiquitous in nature and are widely present in soil, plants, and surface waters. L. monocytogenes, the species most commonly associated with human disease, has been isolated from silage, sewage, slaughterhouse waste, milk from normal and mastitic cows, feces from humans and other, domestic animals (e.g., cattle, sheep, goats, and poultry), insects, and various wild animals. J. M. Farber and P. I. Peterkin, Microbiol. Rev., 55:476-511 (1991); M. L. Gray and A. H. Killinger, Bacteriol. Rev., 30:309-382 (1966); S. A. McCarthy, p. 25-29, in A. J. Miller et al. (eds), Foodborne Listeriosis, (Society for Industrial Microbiology, Elsevier Science Publishing, Inc., New York, 1990); J. Weis and H. P. R. Seeliger, Appl. Microbiol., 30:29-32 (1975). L. monocytogenes has also been recognized as a gastrointestinal tract transient, present in the stool of 5% of the human population. M. N. Swartz, in Microbiology, 4th edition, pp. 717-726 (B. D. Davis et al., eds) (J. B. Lippincott, Philadelphia, 1990).

In ruminants, the central nervous system is primarily affected (causing "circling disease"); septic abortion is a common result of infection of the female reproductive tract. Septicemia and multiple visceral abscesses also occur. As in humans, sporadic cases and epidemic outbreaks have been reported. Thus, while human listeriosis garners the most media attention and is of concern to medical practitioners, the ability to differentiate between Listeria species is also of great importance to veterinary practitioners and those who work to ensure a safe food supply.

Clinical Significance

Because the majority of human listeriosis cases (approximately 70%) occur in individuals with underlying conditions which cause suppression of T-cell mediated immunity, improved characterization of the genus would have important medical consequences. Predisposing conditions often associated with listeriosis include neoplastic disease, immunosuppression, pregnancy, extremes of age (neonates as well as the elderly), diabetes mellitus, cirrhosis, alcoholism, cardiovascular and renal collagen diseases, hematochromatosis, administration of drugs which reduce gastric acidity, frequent transfusions, and hemodialysis failure. R. E. Nieman and B. Lorber, Rev. Infect. Dis., 2:207-227 (1980); Swartz, supra. In a recent study of listeriosis in the United States, researchers estimated a minimum case rate of 90 per 100,000 AIDS patients, a rate 150 times greater than that of the general population in the same age group. B. G. Gellin et al., Am. J. Epidemiol. 133:392-401 (1991).

Although in most immunologically normal adults, the symptoms of listeriosis are relatively mild and flu-like, clinical syndromes include central nervous system infections, primary bacteremia and endocarditis, and infection of various organ systems. J. M. Farber and P. I. Peterkin, Microbiol. Rev. 55:476-511 (1991). Central nervous system infection with L. monocyogenes is typically meningitic or encephalitic, usually presenting with prodromal symptoms of headache, vomiting, fever, and malaise, prior to the appearance of central nervous system infection. Meningitis cases in adults and the elderly are generally associated with a high mortality rate (20-50%) or neurological sequelae in survivors. Bille and Doyle, supra. Due to the strong tropism of L. monocytogenes for the meninges, this organism should be included in the differential diagnosis of meningitis in high-risk groups. In the United States, *L. monocytogenes* is the fifth most common cause of bacterial meningitis; in the past several decades, it has increased four to five-fold in relative frequency underscoring the emerging importance of this organism. Swartz, supra.

In pregnant women, *L. monocytogenes* often causes an influenza-like bacteremic illness, which if unrecognized and untreated may progress to amnionitis and infection of the fetus, resulting in abortion, stillbirth or premature birth of an infected fetus. See Bille and Doyle, supra. Transplacental infection results in disseminated abscessed or granulomas in multiple organs (granulomatosis infantiseptica). Neonatal meningitis and/or bacteremia may result from perinatal bacteremia or from infection acquired during vaginal delivery.

While most human infections are sporadic, there have been several food-borne listeriosis epidemics reported from various countries. Some human listeriosis epidemics have resulted from epizootic outbreaks. For example, one outbreak involved cabbage which had been fertilized with sheep manure obtained from a flock in which many of the animals had died due to listeriosis. Schlech et al., New Eng. J. Med., 308:203-209 (1983). Other listeriosis outbreaks in the North America have been reported from Listeria-contaminated food, including a 1983 milk-associated outbreak (Fleming et al., New Eng. J. Med., 312:404-407 (1985)), and a 1985 outbreak associated with contaminated soft cheese (James et al., Morbid. Mortal. Wkly Rept. 34:357-359 (1985)). There has even been a recent suggestion that listeriosis may be the leading fatal food-borne infection in the United States. B. G. Gellin, supra.

With the need to improve the capability to identify all members of the Listeria genus to the species level, there is also the need to better understand the pathogenicity, if any, associated with each of these particular species. As indicated above, nearly all of the reported cases of human Listeria infections have been caused by *L. monocytogenes*. See McLauchlin, J. Appl. Bacteriol. 63:1 (1987). However, instances have been reported in which *L. ivanovii*, *L. innocua* and *L. seeligeri* have caused disease in humans. See, E. A. Szabo and P. M. Desmarchelier, Epidemiol. Infect. 105:245 (1990); Bille and Doyle, supra.

Isolation and Identification of Listeria From Clinical Specimens

A tentative diagnosis of listeriosis may be made by direct examination of Gram-stained sediment from normally sterile fluids such as cerebrospinal fluid (CSF) or amniotic fluid. Direct examination of Gram-stained clinical specimens is of limited diagnostic value, as Listeria may be present in such low numbers as to go undetected in a stained smear, resulting in a false negative result. Listeria in CSF may be confused with other organisms such as streptococci or corynebacteria, and excessively decolorized organisms may be confused with *Haemophilus influenzae*. Thus, cultures and biochemical tests are required for definitive identification of Listeria.

Blood, CSF, amniotic fluid and tissue biopsies specimens are commonly submitted for Listeria isolation and identification. Clinical specimens obtained from unsterile sites (or any sample which may contain competing flora) should be processed in the same manner as environmental and food specimens. These procedures involve the use of enrichment steps and selective media. Both the Food and Drug Administration (FDA) and the Centers for Disease Control (CDC), have developed enrichment and selective protocols for Listeria isolation and identification.

Tests commonly used in conventional Listeria species identification include observation of beta hemolysis, the CAMP test with *S. aureus* and *R. egui*, nitrate reduction, the Voges-Proskauer test, hydrolysis of cellulose, hippurate and starch, production of lecithinase and phosphatase, acid production (within 1 week) from L-arabinose, dextrin, galactose, glycogen, lactose, D-xylose, mannitol, melezitose, melibiose, L-rhamnose, sorbitol, soluble starch. sucrose, D-xylose, and pathogenicity for mice. Bille and Doyle, supra; H. P. R Seeliger and D. Jones, in *Bergey's Manual of Systematic Bacteriology*, Vol. 2, pp. 1235-1245 (P. H. A. Sneath et. al., eds)- (Williams and Wilkins, Baltimore, 1986); Skalka et. al., J. Clin. Microbiol. 15:503 (1982). Other biochemical tests have been utilized, but have been reported as unsuitable for differentiation between Listeria species, such as fermentation of methyl-D-glucoside. V. H. Seiler and M. Busse, Berl. Munch. Tierärztl. Wsch., 102:166 (1989).

Isolation and Identification of Listeria Food Isolates

Given the ubiquitous nature of this organism and the dire consequences associated with listeriosis in debilitated populations, a major focus has been on disease prevention. An important consideration is the non-existence of a human or veterinary Listeria vaccine. Thus, preventive measures must be undertaken without the safeguards provided by immunization protocols helpful in preventing zoonotic disease outbreaks. As a safe food supply is of utmost concern, methods for the rapid screening of food samples for Listeria are of great importance to the food industry. Under current regulations, the presence of viable cells any Listeria species in foods is cause for alarm.

The FDA and comparable agencies in other countries have promulgated standard laboratory methods to detect the presence of Listeria in environmental or food specimens (e.g., milk). The FDA method is a 7-day enrichment method, (Lovett et al., P17, p. 253, *Abstracts of the Annual Meeting of the American Society for Microbiology*, 1985), while the Centers for Disease Control method is a cold enrichment procedure (Hayes et al., Appl. Environ. Microbiol. 51:438-440 (1986)). These methods involve culturing an appropriately prepared sample on microbiological media under conditions favorable for growth of these organisms and unfavorable for other bacteria. Detection of Listeria species is attempted by examining the morphological and biochemical characteristics of the resultant colonies. This process is typically started 48 hours after acquisition of the sample and requires 9-19 days for completion (if enrichment techniques are required, it will take much longer). See R. L. Buchanan et al., J. Assoc. Off. Anal. Chem., 71:651 (1988); J. Lovett, J. Assoc. Off. Anal. Chem. 71:658 (1988); D. McClain and W. H. Lee, J. Assoc., Off. Anal. Chem. 71:660 (1988); and M. T. Knight et. al., J. Assoc. Off. Anal. Chem. 71: 682 (1988).

Newer methods of detecting Listeria include (a) nucleic acid probes capable of binding to the nucleic acid of particular species, and (b) antibodies capable of reacting with antigens specific to particular species. See e.g., G. Comi et al., Zbl. Hyg. 192:134 (1991); A. R. Datta et. al., Appl. Environ. Microbiol. 54:2933 (1988) (probes to a fragment of a presumptive hemolysin gene of *L. monocytogenes*); J. Klinger, J. Assoc. Off. Anal. Chem. 71:669 (1988) (nucleic acid hybridization assay for Listeria in foods); PCT No. 0355147 (corresponding to U.S. Ser. No. 227,402 and 143,490) (a probe directed to the hemolysin gene in *L. monocytogenes*); European Patent Application No. 0314294 (corresponding to U.S. Ser. No. 965,510) and U.S. Pat. No. 5,089,386 (probes to rRNA of *L. monocytogenes*); U.S. Pat. No. 4,950,589 (monoclonal antibodies directed to a Listeria antigen); G. R. Siragusa and M. G. Johnson, Appl. Environ. Microbiol. 56:1897 (1990) (monoclonal antibodies to an antigen shared with three Listeria species); J. A. Mattingly, J. Assoc. Off. Anal. Chem. 71: 679 (1988) (antibody-based assay for detection of *L. monocytogenes*); European Patent Application No. 0303309 (corresponding to U.S. Ser. No. 836,619) (antibodies to heat-treated extracts of Listeria).

Due to the need for reliable and rapid tests, suitable for a wide range of settings, the suitability of various test kits for Listeria identification has been evaluated. Indeed, the number of test kits and evaluators is testament to the need for the development of a simple, affordable, rapid and reliable method to identify Listeria species. The majority of these kits were originally developed for the identification of other genera. Thus, they are not tailored to the particular needs unique to Listeria identification to the species level. Some require additional tests even to identify a possible Listeria isolate to the genus level.

A. P. MacGowan et al., J. Clin. Pathol. 42:548 (1989), found that API 20 STREP (developed by API-bioMerieux, La Balme des Grottes, France, to identify Streptococcus isolates) identified Listeria in four hours and may be useful for identification of *L. monocytogenes* implicated in human infection. However, they determined that this test kit would not be useful to identify environmental isolates, where identification to the species level is important.

API 50CH (API-bioMerieux, La Balme des Grottes, France) has also been used to identify Listeria and was compared with the API 20 STREP. The utility of API 20 STREP was criticized by Kerr et al., Appl. Environ. Microbiol. 56:657 (1990), for its lack of tests for xylose and rhamnose fermentation, and a-methyl mannosidase activity. These authors were also critical of the large number of substrates used in the API 50CH and the relatively small number of substrates actually relevant in Listeria species identification. The same authors also evaluated the Mast ID system produced by Mast Laboratories (Bootle, United Kingdom). This system utilizes agar plates incorporated with substrates and indicators to determine α-methyl-mannosidase activity, esculin hydrolysis, acetoin production (the Voges-Proskauer test), and fermentation of mannitol, rhamnose, trehalose, salicin and xylose. They found this system to be less expensive than the API 50CH, yet as reliable and rapid (24 hours for results, as opposed to conventional carbohydrate fermentation tests which may require up to 5 days of incubation). However, agar plates containing the appropriate substrates must be prepared prior to inoculation with putative Listeria isolates.

SUMMARY OF THE INVENTION

In one embodiment, the present invention provides a method for detecting a species of the genus Listeria comprising exposing a sample suspected of containing microorganisms belonging to the genus Listeria to a metabolically effective amount of one or more carbon sources selected from the group consisting of tagarose, α-methyl glucoside, L-alanine and/or alanine-peptides, used alone or in combination, capable of being metabolized by a subset of species Listeria species, for a time and under conditions sufficient for said subset to metabolize said carbon source and detecting any metabolism of said carbon source by said microorganisms, thereby determining the presence of said subset of Listeria species.

In another embodiment, the method further comprises, prior to the exposing step, subjecting the sample to an enrichment treatment which will enhance the population of the genus Listeria in the sample.

The present invention contemplates use of a panel of carbon sources comprised of tagatose, α-methyl glucoside, L-alanine and/or alanine-peptides. In one embodiment, the alanine-peptides comprise a peptide cocktail.

The present invention also contemplates a test kit for the detection of a species of the genus Listeria or a strain of a species of the genus Listeria comprising at least one compartment containing at least one carbon source capable of being metabolized by a subset of species of the genes Listeria, wherein the carbon source is selected from the group consisting of tagatose, a-methyl glucoside, L-alanine and/or alanine-peptides.

The present invention further provides a method for detecting a species of the genus *L. welshimeri* comprising exposing a sample suspected of containing microorganisms belonging to the genus Listeria to a metabolically effective amount of one or more carbon sources capable of being metabolized by *L. welshimeri* but not metabolized by other species of Listeria, for a time and under conditions sufficient for metabolism by *L. welshimeri* and detecting any metabolism of said carbon source, thereby determining the presence of *L. welshimeri*. In one embodiment of this method, the carbon source is D-tagatose.

In another embodiment of the method, the method further comprises, prior to the exposing step, subjecting the sample to an enrichment treatment which will enhance the population of the genus Listeria in the sample.

The present invention also contemplates a method for distinguishing between the species *L. innocua* and *L. monocytogenes* or comprising exposing a sample suspected of containing said microorganisms *L. innocua* and/or *L. monocytogenes* to a metabolically effective amount one or more carbon sources capable of being metabolized by *L. innocua* but not metabolized by *L. monocytogenes* for a time and under conditions sufficient for metabolism by said subset of species and detecting any metabolism of said carbon source, thereby determining the presence of a species other than *L. monocytogenes*. In one embodiment of this method, the carbon source is L-alanine and/or alanine-peptides.

In one embodiment of this method, the method further comprises, prior to the exposing step, subjecting the sample to an enrichment treatment which will enhance the population of the genus Listeria in the sample.

The present invention also contemplates a method for distinguishing between *L. monocytogenes* and/or *L. innocua* comprising exposing a sample suspected of containing said microorganisms *L. monocytogenes* and *L. innocua* to a metabolically effective amount of one or more carbon sources capable of being metabolized by *L. monocytogenes* but not by *L. innocua* for a time and under conditions sufficient for metabolism by said subset of species and detecting any metabolism of said carbon source, thereby determining the presence of a species other than *L. innocua*. In one embodiment of this method, the carbon source is α-methyl glucoside.

In one embodiment of this method, the method further comprises, prior to the exposing step, subjecting the sample to an enrichment treatment which will enhance the population of the genus Listeria in the sample.

In a preferred embodiment, the method comprises a method for detecting a species of the genus Listeria comprising exposing a sample suspected of containing microorganisms belonging to the genus Listeria to a metabolically effective amount of one or more carbon sources selected from the group consisting of D-xylose, L-rhamnose, α-methyl-D-mannoside, mannitol, glucose-1-phosphate, α-methyl-D-glucoside, tagatose, 5' AMP, and a combination of alanine-peptides in a peptide cocktail (alanyl-alanine, alanyl-methionine, and alanyl-valine) capable of being metabolized by a subset of species Listeria species, for a time and under conditions sufficient for said subset to metabolize said carbon source and detecting any metabolism of said carbon source by said microorganisms, thereby determining the presence of said subset of Listeria species.

This invention also contemplates a test kit for the detection of a species of Listeria or a strain of a species of the genus Listeria, comprising a plurality of compartments containing at least a plurality of carbon sources capable of being metabolized by a subset of species of the genus Listeria, each carbon source of said panel in separate compartments, wherein the carbon source is selected from the group consisting of D-xylose, L-rhamnose, α-methyl-D-mannoside, mannitol, glucose-1-phosphate, α-methyl-D-glucoside, tagatose, 5' AMP, and a peptide cocktail comprised of alanine-peptides (alanyl-alanine, alanyl-methionine, and alanyl-valine).

This invention further contemplates an enrichment medium for species of the genus Listeria comprising, in liquid or semi-solid form, a basal medium having all the constituents selective for growth of the genus Listeria, and a growth effective amount of one or more carbon sources capable of being utilized by a subset of species of the genus Listeria, wherein the carbon source is selected from the group consisting of tagatose, α-methyl glucoside, and L-alanine and/or alanine-peptides used alone or in a peptide cocktail.

Conclusion

While recently developed methods are useful in the detection of Listeria species, the present invention provides methods and compositions which will be useful in a wide variety of settings, ranging from the research bench, to the clinical, public health and veterinary laboratory, as well as in the field, a setting in which complicated and environment-sensitive equipment and methods are precluded. The direct use of this invention with sample material is contemplated, as is the use of this invention in conjunction with traditional enrichment methods (e.g., cold enrichment procedures) for Listeria.

The present invention provides refinements of capable of (1) detecting bacteria of the genus Listeria and (2) distinguishing between species of the genus Listeria. The method of the present invention has the advantage over previous methods in that it is easier, simpler and less expensive. It is also faster than the current biochemical characterization procedures which involve detection oil slow fermentation reactions, observed through use of pH indicators. Thus, this invention represents a major contribution to the study of Listeria, including species veterinary and medical importance.

DETAILED DESCRIPTION OF THE INVENTION

The present invention is predicated in part on the discovery that differential metabolism of a variety of novel carbon sources may be used to differentiate between even the most closely related species of the genus Listeria. Thus these methods may be used to not only distinguish members of the genus Listeria from other microorganisms, but to distinguish between isolates of different species. The present invention is also based on the discovery that specific strains within the genus Listeria can be distinguished from other strains of the same species by differential metabolism of a variety of carbon sources.

The present invention contemplates that the differential metabolism can be observed at the biochemical level by measuring parameters such as respiration fermentation (e.g., measured colorimetrically) and microbial growth (e.g., measured turbidimetrically). The present invention also contemplates that this differential metabolism can also be observed by (a) using an indicator strain of Listeria that is competent for transformation, (b) using nucleic acid probes, or (c) employing specific antibodies.

Unless otherwise specified, the generic term "Listeria" is used herein to refer to all species of the genus including, but not limited to, L. monocytogenes, L. ivanovii, L. innocua, L. welshimeri, L. seeligeri, L. grayi, and L. murrayi.

With respect to the phrase "microorganisms suspected of being of the genus Listeria" it is not meant that the microorganisms must be homogeneous. It may comprise a heterogeneous mixture of Listeria species or strains of one or more species of Listeria and may contain microorganisms not belonging to the genus Listeria. On the other hand, it may comprise homogenous and/or substantially pure cultures of one or more species or strains of Listeria.

The term "sample" in the present specification and claims is used in its broadest sense. On the one hand it is meant to include a specimen or culture. On the other hand, it is meant to include both biological and environmental samples.

Biological samples may be animal, including human, fluid or tissue, food products and ingredients such as dairy items, vegetables, meat and meat by-products, and waste. Environmental samples include environmental material such as surface matter, soil, water and industrial samples, as well as samples obtained from food and dairy processing instruments, apparatus, equipment, disposable and non-disposable items. These examples are not to be construed as limiting the sample types applicable to the present invention.

whether biological or environmental, a sample suspected of containing Listeria may or may not first be subjected to an enrichment means to create a culture of microorganisms suspected of being of the genus Listeria. By "enrichment means" or "enrichment treatment," the present invention contemplates (i) conventional techniques for isolating Listeria away from other microorganisms and (ii) novel techniques for isolating Listeria away from other microorganisms, involving the use of one or more of the carbon sources of the present invention. Importantly, it is not intended that the present invention be limited only to one enrichment step or type of enrichment means. For example, it is within the scope of the present invention to, following subjecting a sample to a conventional enrichment means, subjecting the resultant preparation to further purification such that pure or substantially pure cultures of Listeria species or strain of species are produced. With respect to a "culture" it is not meant that the enrichment means must only be in a liquid phase. The present invention contemplates a variety of types of enrichment means (whether in or on a liquid, solid or semi-solid medium).

The carbon compounds of choice in accordance with the present invention are those which some species of the genus Listeria can utilize as a carbon source for growth, respiration, or fermentation, but which are unable or substantially unable to be metabolized by other species of the same genus. Utilization of carbohydrates tested in combination is also contemplated (e.g., a mixture of D-gluconic acid, L-maltose and mannitol). In addition to carbohydrates and alcohols, other compounds such as peptides of varying lengths (e.g., dipeptides composed of alanine and another amino acid, such as aspartic acid, glutamic acid, glutamine, histidine, lysine, phenylalanine, proline, glycine, valine, leucine, isoleucine, alanine and methionine) are contemplated as carbon sources. Use of a "peptide cocktail" is contemplated. As used herein, a "peptide cocktail" refers to a mixture of two or more peptides tested in combination.

In one embodiment, the present invention involves using L-lactic acid and/or a hexose phosphate (e.g., glucose-phosphate, mannose-phosphate and fructose-phosphate) as carbon sources of choice. Where a hexose phosphate is used. glucose-1-phosphate is a preferred sugar phosphate (primarily because of its stability, purity and commercial availability). Such carbon sources have heretofore never been reported useful for Listeria detection or identification to the species level.

In another embodiment, the present invention also describes the use of xylitol as a carbon source. Xylitol (to be distinguished from D-xylose) is a carbon source heretofore never reported useful for Listeria detection or identification to the species level.

In another embodiment, the present invention also describes the use of adenosine 5'-monophosphate (5'AMP) as carbon source. 5'AMP is a carbon source heretofore never reported useful for Listeria detection or identification to the species level.

In another embodiment, the present invention also describes the use of glycerol, β-methyl glucoside, D-gluconic acid and/or L-malic acid as carbon sources. Heretofore, it was reported that all of the species could utilize glycerol and α-methyl glucoside, that none of the Listeria species could utilize gluconic acid, and that malic acid was primarily utilized by *L. monocytogenes*. Wilkinson and Jones, supra. Our findings are not in agreement with many aspects of this report. In the case of malic acid, the report indicates that a mixture of the D- and L-isomers was used. The usefulness of β-methyl glucoside for identification of Listeria to the species level has not heretofore been reported.

In one embodiment, the present invention involves using tagarose, α-methyl glucoside, L-alanine and/or alanine-peptides and/or peptide cocktails as the carbon sources of choice.

The present invention describes the use of the above-named carbon sources together with one or more carbon sources heretofore tested in the detection and/or identification of Listeria (e.g., L-lactic acid, glucose-1-phosphate, xylitol, D-gluconic acid, L-malic acid, 5'AMP, glycerol, β-methyl glucoside, mannitol, L-rhamnose, D-xylose, sucrose, α-D-lactose and L-rhamnose). This is done, however, with the understanding that it is not intended that the present invention be limited to the use of known useful Listeria carbon sources in conjunction with the novel sources described earlier. Furthermore, the present invention extends to chemical, biochemical, biological and/or functional equivalents or homologues of the aforementioned carbon sources including any structural modifications thereto provided that said equivalents, homologues or modified carbon sources are utilized by some species of the genus Listeria. The carbon sources of the present invention may also be added as the corresponding salts.

The carbon sources may be used singularly or in combination with other carbon sources. However, in some circumstances, two or more carbon sources may not be appropriate in combination due to catabolite repression or utilization by other non-Listeria organisms.

Antibiotics or other selective agents (e.g., lithium salts) may be used in conjunction with the present invention to inhibit non-Listeria organisms and/or to promote growth of Listeria.

A preferred embodiment of the present invention contemplates a method for detecting species of the genus Listeria in a biological sample comprising, subjecting said sample to an enrichment means so as to create a pure culture of microorganisms suspected of being of the genus Listeria exposing said culture separately or together to amounts of carbon sources effective for metabolism, wherein the carbon sources are selected from the group consisting of tagatose, n-methyl glucoside, L-alanine and/or alanine-peptides (particularly alanyl-alanine, alanyl-methionine and alanyl-valine), and wherein the exposure is for a time and under conditions sufficient for metabolism, and then detecting metabolism.

Another preferred embodiment of the present invention contemplates a method for detecting a species of the genus Listeria in a biological sample comprising, subjecting said sample to an enrichment means so as to create a culture of microorganisms suspected of being of the genus Listeria, exposing said culture to a panel of carbon sources consisting of L-lactic acid, glucose-1-phosphate, xylitol, D-gluconic acid, L-malic acid, 5'AMP, glycerol, and β-methyl glucoside, wherein the carbon sources are in amounts effective for metabolism and wherein said exposure is for a time and under conditions sufficient for metabolism and detecting metabolism.

Another preferred embodiment of the present invention contemplates a method for detecting a species of the genus Listeria in a biological sample comprising, subjecting said sample to an enrichment means so as to create a culture of microorganisms suspected of being of the genus Listeria, exposing said culture to a panel of carbon sources consisting of mannitol, L-lactic acid, glucose-1-phosphate, xylitol, 5'AMP, β-methyl glucoside, L-rhamnose, D-xylose, and alpha-methyl mannoside, wherein the carbon sources are in amounts effective for metabolism and wherein said exposure is for a time and under conditions sufficient for metabolism, and detecting metabolism.

Another preferred embodiment of the present invention contemplates a method for detecting a species of the genus Listeria in a biological sample comprising, subjecting said sample to an enrichment means so as to create a culture of microorganisms suspected of being of the genus Listeria, exposing said culture to a panel of carbon sources consisting of tagatose, α-methyl glucoside, L-alanine and/or alanine-peptides, wherein the carbon sources are in amounts effective for metabolism and wherein said exposure is for a time and under conditions sufficient for metabolism, and detecting metabolism.

In the practice of the present invention it has been found that L-lactic acid and glucose-1-phosphate as carbon sources are useful to differentiate *L. monocytogenes* and *L. ivanovii* from *L. innocua, L. welshimeri, L. seeligeri, L. grayi*, and *L. murrayi*; xylitol as a carbon source is useful to differentiate *L. monocytogenes, L. innocua, L. welshimeri* and *L. seeligeri*, from *L. ivanovii, L. grayi*, and *L. murrayi*; 5'AMP, D-xylose, mannitol, D-gluconic acid and L-malic acid are useful as carbon sources to differentiate *L. grayi* and *L. murrayi* from *L. monocytogenes, L. ivanovii, L. innocua, L. welshimeri* and *L. seeligeri*; L-rhamnose as a carbon source is useful to distinguish *L. monocytogenes, L. innocua* and *L. welshimeri*, from other species of Listeria. Lastly, glycerol and β-methyl glucoside as carbon sources are useful to distinguish *L. ivanovii* and *L. grayi* from other species of Listeria since they give a negative or a very weak positive reaction with these. (See Table 1).

In the practice of the present invention it has been found that D-tagatose is useful to distinguish *L. welshimeri* (which is able to utilize tagatose), from the other Listeria species (which are unable to utilize tagatose). Also, it has been found that α-methyl glucoside is used to distinguish between *L. monocytogenes* (which is able to utilize this compound) and *L. innocua* (which is unable to utilize this compound).

In accordance with one embodiment of the present invention, the carbon sources are added to a reaction vessel containing basal medium and other constituents as required for growth. "Basal medium" as used herein refers to a medium suitable for growth of Listeria but which does not contain sufficient amounts of a carbon source for metabolism. More conveniently, the carbon sources are added separately or in combination into a series of reaction vessels such that a range of carbon sources and/or various combinations of carbon sources can be tested at one time. Alternatively, the reaction vessel(s) may contain the required carbon source to which basal medium is then added or the carbon source may be added to the basal medium already in the reaction vessel. The order of addition of the components in accordance with the present invention is not critical. In addition to the carbon source and basal medium and other components necessary for growth, each reaction vessel may also contain one or more indicator molecules such as, but not limited to, a redox indicator (e.g., tetrazolium), a pH indicator, and various dyes and the like. These approaches are fully described in U.S. Pat. Nos. 4,129,483 and 4,235,964 to Barry R. Bochner, hereby incorporated by reference. A generalized indicator useful for practice of the present invention is also described by Bochner and Savageau. See B. Bochner and M. Savageau, Appl. Environ. Microbiol., 33:434 (1977).

Analysis of differential carbon source metabolism as contemplated herein is conveniently conducted using a test kit. In a preferred embodiment of the present invention, the test kit comprises a microtiter plate containing an appropriate basal medium. The required carbon source is then added to each compartment at the appropriate concentration. Each compartment may, along with the basal medium, also contain an appropriate indicator or the compartment may be so constructed that growth is measurable turbidimetrically. Alternatively, the indicator may be added separately. In any event, the preferred use of the basal medium, carbon source, indicator and any other chemical (or mixture of chemicals) is in a dry form in the microplate.

It is preferred in this case, that the microorganisms suspected to be Listeria are prepared as required in saline or other suitable diluent and then each compartment of the plate inoculated.

Plates useful in the practice of the present invention as a kit are commercially available from Biolog, Inc., Hayward, Ca. For example, the Biolog MT MicroPlate ™ is particularly useful. The MT plate is a 96-well microplate designed to test the ability of an inoculated microorganism suspension to utilize (oxidize) a panel of different carbon sources. Each well of the panel contains a tetrazolium redox dye and a buffered nutrient medium that has been developed and optimized for a wide variety of bacteria. If used in the practice of the present invention, the carbon sources of the present invention may be added to the MT plates either before or after inoculating with a microorganism suspension. For example, with a Biolog MT MicroPlate ™, about 0.6 mg of carbon source (e.g., 15 μl of a 4% stock solution) may be added to each well giving a resulting concentration of 0.4% (w/v). The preferred concentration for alpha-methyl glucoside is 0.27%. Other substrate concentrations are also contemplated. After addition the carbon source may be dried. The Biolog's MT MicroPlate ™ may be arranged so that there is one or more negative control wells with no carbon source and/or one or more positive control wells containing a carbon source (e.g., salicin) or a mixture of carbon sources such that all Listeria strains will give a positive reaction. The remaining wells of a set contain individual carbon sources or a combination of carbon sources that may or may not be metabolized. After inoculation, the reaction vessel, compartment or indicator plate is then incubated at an appropriate temperature or range of temperatures, preferably between 25–40° C. and most preferably between 30–37° C. for 1 to 24 hours. Many of the carbon source reactions are apparent even by 1 hour.

As noted earlier, a sample suspected of containing Listeria may be first subjected to an enrichment means and this enrichment means may involve (i) conventional techniques for isolating Listeria away from other microorganisms or (ii) novel techniques for isolating Listeria away from other microorganisms involving the use of one or more of the carbon sources of the present invention.

Where conventional techniques are used in the enrichment step, a sample suspected to contain one or more species of Listeria may be inoculated onto a semi-solid medium (e.g., an agar plate) as an enrichment means. The inoculated semi-solid medium is then optionally exposed to conditions which allow for growth of the Listeria. Conventional enrichment means may be selected from any available to those skilled in the art, including bun not limited to, the following: original McBride Listeria agar formulations, modified McBride Listeria agar formulation, LiCl-phenylethanol-moxalactam (LPM) agar, acriflavine-ceftazidime agar, Rodriguez isolation agar (RISA), modified Vogel-Johnson (MVJ) agar and cyclohexanedione-nalidixic acid-phenylethanol agar and their liquid forms. Most preferably, the enrichment means is LPM or MVJ. A general discussion of other suitable media for Listeria can be found in Loessner et al., Appl. Environ. Microbiol., 54:3003 (1988); Buchanan et al., Appl. Environ. Microbiol., 55:599 (1989); Lachica, Appl. Environ. Microbiol., 56:167 (1990).

Where novel techniques of the present invention are used in the enrichment step, a sample suspected to contain one or more species of Listeria may be inoculated onto a semi-solid medium (e.g., an agar plate). The inoculated semi-solid medium is then optionally exposed to conditions which allow for growth of the Listeria. In any event, microorganisms present on the plate may then be re-plated or transferred to liquid or semi-solid growth media containing a carbon source of the present invention which may be utilized by one or more species of Listeria but not by other species of the same genus.

Alternatively, using novel enrichment techniques of the present invention, the sample may be inoculated directly into or onto a liquid or semi-solid growth medium containing, as sole carbon source, a carbon source of the present invention capable of being utilized by one or more species of Listeria but not by other species of the same genus.

In one embodiment, utilization of a carbon source is measured by the formation of one or more colonies of the pathogenic strain. The amount of carbon source added to the reaction vessel will be that required for growth of Listeria. By "growth" it is meant that the bacterial population has undergone at least one doubling, the only requirement being that sufficient doubling must take place in order for the particular indicator to detect growth, or for there to be sufficient growth to be measured turbidimetrically. When a semi-solid growth medium is used, sufficient growth is required to observe one or more colonies. Typically, the final concentration of carbon source is from about 0.05 to about 5.0% (w/v) and preferably from about 0.20 to about 1.0% (w/v). Most preferably, the concentration of carbon source is approximately 0.4% (w/v). However, the concentration may be varied depending on the organism to be detected, availability of carbon source, ease of solubility and indicator selected.

According to this embodiment of the present invention, there is provided an enrichment or selection growth medium for one or more species of Listeria comprising in liquid or semi-solid form, a basal medium having all the constituents required for growth of Listeria except for a carbon source and a growth effective amount of one or more carbon sources capable of being utilized by one or more species of Listeria but not by other species of the same genus.

The present invention also contemplates a novel enrichment means wherein the aforementioned conventional media are used, but wherein the principle carbon source is replaced by one or more of the carbon sources of the present invention.

Other Detection Methods

As noted earlier, the present invention contemplates that the differential metabolism can be observed at the metabolic or biochemical level by measuring parameters such as respiration (e.g., measured colorimetrically) and microbial growth (e.g., measured turbidimetrically). On the other hand, the present invention contemplates that this capability for differential metabolism can also be observed by other detection methods including a) using an indicator strain of Listeria in a genetic repair assay, b) using nucleic acid probes in a hybridization assay, or c) employing specific antibodies in an immunological assay or strain.

a) Genetic Repair Assay

Another assay contemplated by the present invention allows the rapid screening of biological samples for the presence or absence of pathogenic strains of Listeria. The assay provides a simple yes/no test whether or not a biological sample, such as food, contains a pathogenic strain of Listeria.

In one embodiment, an indicator strain of Listeria is rendered competent for transformation by naked DNA and also carries a mutation affecting expression of one or more enzymes or other proteins involved in the uptake or metabolism of a carbon source by pathogenic strains of Listeria and which carbon sources are not metabolized by non-pathogenic strains of Listeria (examples of such carbon sources may be L-lactic acid or hexose-phosphate; see Table 2 and accompanying discussion, below). The indicator strain may also express a selective marker such as but not limited to resistance to an antibiotic or other antimicrobial compound including a heavy metal. The biological sample is then subjected to genetic extraction meaning that the DNA of any microorganism therein is released by such means as enzymes, organic extraction, detergents or sonic disruption. Further purification and partial digestion of the genetic extract may then be required depending on the biological sample, time and degree of sensitivity desired.

The genetic extract is then mixed with an excess of the competent indicator strain for a time and under conditions sufficient to allow transformation of the indicator strain with any Listeria DNA. The mixture is then added dropwise or by other means to the semi-solid or liquid medium. The mixture is introduced to the medium containing, as sole carbon source, the carbon source on which the mutation it carries prevents it from growing. The medium is then incubated and examined for growth. If growth does occur, the indicator strain must have been transformed with DNA from a pathogenic strain and the mutation preventing the indicator strain from growing on the sole carbon source in the medium repaired. Appropriate controls are also run to verify that the genetic lesion did not revert and that the sample extract containing DNA was not contaminated with viable microorganisms.

Many variations to the above assay may be made without departing from the scope of the present invention. For example, rather than the DNA entering the indicator strain by transformation, it might enter by transduction following an in vitro phage packaging reaction, or by conjugation, possibly with a non-Listeria competent strain that would take up naked DNA and transfer it by conjugation into the Listeria indicator strain. In the latter case, the growth medium may additionally contain an agent to prevent growth of the non-Listeria bacterium. Transformation techniques are disclosed, for example, in U.S. Pat. Nos. 3,930,956 and 4,038,143 to E. Juni, hereby incorporated by reference. Other approaches are disclosed in A. Janik et. al., J. Clin. Microbiol. 4:71 (1976). Transformation techniques for Listeria are disclosed in R. D. Lucas and R. E. Levin, Lett. Appl. Microbiol. 9:215 (1989).

Accordingly, this aspect of the present invention contemplates a means for detecting a potentially pathogenic strain of a species of the genus Listeria in a biological or environmental sample comprising 1) providing a competent strain of Listeria carrying a mutation in or near a gene encoding an enzyme or other protein or parts thereof involved in or associated with the uptake or metabolism of a carbon source used by a potentially pathogenic strain of Listeria, or in or near a promoter region, regulatory gene or other control sequence or parts thereof for expression of said enzyme or other protein, said mutation resulting in said enzyme or other protein not being produced or being produced in inactive form, thereby said competent strain of Listeria being unable to grow on said carbon source, 2) contacting said competent strain of Listeria carrying said mutation with a genetic extract of said biological or environmental sample for a time and under conditions sufficient for said competent strain of Listeria to be transformed with DNA of a potentially pathogenic strain of Listeria, if present, in said genetic extract of the sample, wherein said DNA is capable of repairing the mutation in said competent strain of Listeria and 3) detecting growth of said transformed Listeria on the carbon source for which previously the strain could not grow.

Another aspect of the present invention provides a means for detecting a potentially pathogenic strain of a species of the genus Listeria in a biological or environmental sample comprising 1) providing an indicator strain of Listeria carrying a mutation in or near a gene encoding an enzyme or other protein or parts thereof involved in or associated with the metabolism of a carbon source used by a potentially pathogenic strain of Listeria, or in or near a promoter region, regulatory gene or other control sequence or parts thereof for expression of said enzyme or other protein, said mutation resulting in said enzyme or other protein not being produced or being produced in inactive form, thereby said indicator strain of Listeria being unable to grow on said carbon source, 2) contacting said indicator strain of Listeria carrying said mutation with a conjugative donor strain or a phage for a time and under conditions sufficient for said indicator strain of Listeria to be conjugated or transduced with DNA from a potentially pathogenic strain of Listeria, if present, in said sample, wherein DNA transferred is capable of repairing the mutation in said indicator strain of Listeria, and 3) detecting growth of said repaired Listeria on the carbon source for which previously the strain could not grow.

b) Hybridization Assay

Another embodiment of the present invention relates to a nucleic acid molecule capable of hybridizing to genetic material contained in a genetic extract of one or more species of the genus Listeria but which does not hybridize to genetic material in other species of the same genus. Ideally, the nucleic acid molecule will hybridize under predetermined stringency levels to genetic material, at least part of which, encodes an enzyme or protein or portions thereof or defines a promoter region, regulatory gene or other control sequence or parts thereof for expressing enzymes or other proteins associated with the metabolism by particular species of Listeria of the aforementioned carbon source compounds, said genetic material substantially absent in other species of the same genus.

In this regard, the genetic material may be DNA or RNA. When the genetic material is mRNA, the bacterial cells may first need to be inoculated in the presence of the subject carbon source for a time and under conditions sufficient to permit transcription of the DNA into mRNA. A genetic extract comprises the genetic material (i.e., DNA or RNA) or various parts thereof from a particular cell.

"Hybridization" is used herein in its broadest sense and refers to the formation of duplexes between completely or partially complementary nucleotide sequences by Watson-Crick base-pairing. The stringency conditions used may very depending on the base composition of the probe-Larger duplex as well as by the level and geometry of mispairing between the two nucleic acids.

The genetic detection of a species of Listeria may be accomplished in a number of ways. In one preferred embodiment, the species or strain to be identified is grown on semi-solid media into one or more colonies. The colonies are transferred onto nitrocellulose paper or other suitable material and subjected to dot blot analysis or similar hybridization procedure. Techniques useful for this type of genetic screening can be found in Sambrook et al., (eds), *Molecular Cloning: A Laboratory Manual*, 2d edition, (Cold Spring Harbor Laboratory, Cold Spring Harbor, N.Y., 1989).

The nucleic acid probes may be prepared by any number of means. For example, an enzyme or protein involved in or associated with the metabolism of a carbon source by one or more species of Listeria and which is absent from other species of the same genus is first purified and a contiguous series of amino acids in said enzyme or other protein determined. For example, the N-terminal amino acid sequence is ascertained and a probe comprising nucleotide sequence is the prepared based on the amino sequence. Generally a range of probes is produced. Using Southern or Northern blots, a probe capable of hybridizing to genetic material in one or more species of Listeria but not genetic material from other species is selected.

Conveniently, a biological sample may be screened for the presence of a species of Listeria by immobilizing bacteria contained in said biological sample onto a semi-solid support and then subjecting said immobilized bacteria to detection means by using a labelled nucleotide probe. The label may be a radioactive isotope, or biotinylated molecule or other detectable marker.

This aspect of the present invention is conveniently provided in kit form comprising a compartment or a multiplicity of compartments adapted to receive a biological sample suspected to contain a species of Listeria, a second compartment or multiplicity of compartments adapted to contain one or more nucleic acid molecules capable of hybridizing at pre-determined stringency conditions to genetic material encoding one or more enzymes or other protein or portions thereof or defining a promoter region, regulatory gene or other control sequence or parts thereof for expressing enzymes or other proteins involved in or associated with the metabolism of one or more carbon sources by one or more species of Listeria and which genetic material is absent or substantially absent from another species of the same genus, said nucleic acid molecules labelled with a reporter molecule.

In further accordance with this aspect of the present invention, the sensitivity and/or ease of performing this assay may be enhanced by using the polymerase chain reaction (PCR) as described by K. B. Mullis et al., in U.S. Pat. Nos. 4,683,195 and 4,683,202, hereby incorporated by reference. To this end, the present invention extends to nucleotide probes or primers useful in the PCR to detect the aforementioned DNA or RNA. Accordingly, the kit contemplated herein may contain additional compartments adapted to contain the components for PCR including the nucleotide primers.

c) Immunological Assay

A further aspect of the present invention relates to the immunological detection of a species of Listeria using antibodies directed to an enzyme or other protein present in said species but absent in other species of the same genus and which are involved in or associated with the utilization of one or more carbon sources, said enzyme or protein absent in said other species of the same genus. The enzyme or protein is purified from the species by conventional techniques and used to prepare specific antibodies. Such antibodies are useful in developing detection assays (immunoassays) for the enzyme or protein. The presence of the enzyme or protein in a biological sample or an extract thereof is indicative of the presence of a species of Listeria.

In the following methods, where specific enzymes or proteins are not secreted from the bacterium to be detected, the cells are disrupted by treatments which include sonic disruption, osmotic change or use of agents such organic solvents, detergents, enzymes and the like.

Furthermore, immunological equivalents of the enzymes or proteins may be used to facilitate the production of antibodies. Additionally, a mixture of enzymes or proteins may be used to facilitate the production of antibodies. A mixture of enzymes or proteins may also be used to develop antibodies.

The antibodies may be monoclonal or polyclonal. It is within the scope of this invention to include any second antibodies (monoclonal or polyclonal) directed to the first antibodies discussed above. Both the first and second antibodies may be used in the detection assays or a first antibody may be used with a commercially available anti-immunoglobulin antibody. An antibody as contemplated herein includes any antibody specific to any region of an enzyme or other protein exclusively involved in the metabolism of a carbon source by one or more species of Listeria and which is absent from another species of the same genus.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of the purified enzyme or protein, or antigenic parts thereof, collecting serum from the animal, and isolating specific sera by any of the known immunoadsorbent techniques. Although antibodies produced by this method are utilizable in virtually any type of immunoassay, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example J. Douillard and T. Hoffman, in *Compendium of Immunology*, Vol. II, (Schwartz, ed., Van Nustiand Reinhold, 1981); G. Kohler and C. Milstein, Nature 256:495 (1975); G. Kohler and C. Milstein, Eur. J. Immunol., 6:511 (1976).

Unlike preparation of polyclonal sera, the choice of animal is dependent on the availability of appropriate immortal lines capable of fusing with lymphocytes. Mice and rats have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with an antigenic amount, for example, from about 0.1 mg to about 20 mg of the enzyme or protein or antigenic parts thereof. Usually the injecting material is emulsified in Freund's complete adjuvant. Boosting injections may also be required. The detection of antibody production can be carried out by testing the antisera with appropriately labelled antigen. Lymphocytes can be obtained by removing the spleen or lymph nodes of sensitized animals in a sterile fashion and carrying out fusion. Alternatively, lymphocytes can be stimulated or immunized in vitro, as described, for example, in C. L. Reading, J. Immunol. Meth., 53:261 (1982).

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin.

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1000 to 6000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion can be useful. The ratio between lymphocytes and malignant cells is optimized to avoid cell fusion among spleen cells and a range of from about 1:1 to about 1:10 is commonly used.

The successfully fused cells can be separated from the myeloma line by any technique known by the art. The most common and preferred method is to choose a malignant line which is Hypoxanthine Guanine Phosphoribosyl Transferase (HGPRT) deficient, which will not grow in an aminopterin-containing medium used to allow only growth of hybrids and which is generally composed of hypoxanthine $1 \times 10^{-4}$M, aminopterin $1 \times 10^{-5}$M, and thymidine $3 \times 10^{-5}$M, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxanthine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21-23 of cell growth in selected medium. Cloning can be performed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semi-solid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8-12 days after intraperitoneal injection. The ascites contain a higher concentration of antibodies but include both monoclonals and immunoglobulins from the inflammatory ascites. Antibody purification may then be achieved by, for example, affinity chromatography.

The presence of the enzyme or protein contemplated herein in a species of Listeria may be accomplished in a number of ways such as on a semi-solid growth medium plate where colonies of bacteria are tested, by for example, the Western blotting procedure. Alternatively, other semi-solid supports may be employed onto which the biological sample has been immobilized. In another method, the biological sample is contacted with a solid support already containing a specific antibody. In any event the principle behind the assay is the same. A wide range of immunoassay techniques are available as can be seen by reference to U.S. Pat. Nos. 4,016,043, 4,424,279 and 4,018,653. This, of course, includes both single-site and two-site, or "sandwich", assays of the non-competitive types, as well as in the traditional competitive binding assays.

Sandwich assays are among the most useful and commonly used assays and are favored for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen secondary complex, a second antibody specific to the antigen, labelled with a reporter molecule capable of producing a detectable signal is then added and incubated, allowing time sufficient for the formation of a tertiary complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent.

In the typical forward sandwich assay, a first antibody having specificity for the enzyme or protein, or antigenic parts thereof, contemplated in this invention, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated at 25° C. for a period of time sufficient to allow binding of any subunit present in the antibody. The incubation period will vary but will generally be in the range of about 2–40 minutes. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores, luminescent molecules or radionuclide containing molecules (i.e., radioisotopes).

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine, 5-aminosalicylic acid, or toluidine are commonly used. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the tertiary complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is when exposed to the light of the appropriate wavelength the fluorescence observed indicates the presence of the hapten of interest. Immunofluorescent and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

Accordingly, an aspect of the present invention contemplates a method for detecting a species of the genus Listeria in a biological sample comprising the steps contacting said biological sample with an antibody to an enzyme or other protein or parts thereof wherein said enzyme or other protein is involved in or associated with the metabolism of a carbon source in a species of Listeria and which is absent from another species of same genus for a time and under conditions sufficient for an enzyme- or other protein-antibody complex to form and subjecting said complex to a detecting means. The present invention contemplates that the antibody binding can be visualized by a number of methods including fluorescent staining.

In accordance with this method, the target bacteria or extracts thereof may first be immobilized onto a solid support. Where the target bacteria is immobilized, solid supports such as slides, plates, filters, beads or the like may be used. Where extracts such as protein are immobilized, solid supports such as resins can be used (resins are readily available commercially). On the hand, protein may also be immobilized on supports such as those mentioned above for bacteria.

The present invention is also directed to a kit for the rapid and convenient assay for species of Listeria in a biological sample. The kit is compartmentalized to receive a first container adapted to contain a biological sample to be tested and a second container adapted to contain an antibody to an enzyme or protein of species of Listeria as defined above, said antibody being labelled with a reporter molecule capable of giving a detectable signal as hereinbefore described. Alternatively, if said first antibody is not labelled then a further container is provided adapted to contain a second antibody to said first antibody where said second antibody is labelled with a reporter molecule. If the reporter molecule is an enzyme, then another container adapted to contain a substrate for said enzyme is provided.

Whether by a) genetic repair, b) hybridization, or c) antibody binding, the above three detection approaches require identification of enzymes, proteins or portions thereof, or identification of nucleic acid defining a promoter region, functional gene, regulatory gene or other control sequence or parts thereof for the expression of enzymes or other molecules involved in differential uptake or metabolism of the carbon sources of the present invention. Some enzymes involved in uptake or metabolism of some of these carbon sources are already known (e.g., L-lactic acid dehydrogenase, L-lactic acid oxidase, hexose phosphate phosphatase, etc.). Mutants deficient in some of these enzymes (and thus useful for transformation assays) are also known. See F. Mat-Jan et al., J. Bacteriol., 171:342 (1989). Furthermore, nucleotide sequences of the genes for some enzymes (useful for the design of probes in hybridization assays) are described. E. Pradel et al., J. Bacteriol., 172:802 (1990). Finally, such enzymes nave been purified and antibodies have been raised against them (useful in immunological assays). M. Fatai and H. Kimura, J. Biol. Chem., 252:5820 (1977).

The present invention is further described by the following non-limiting Examples.

EXAMPLE ONE

Detection and Identification of Listeria to the Species Level by Differential Carbon Source Metabolism Using the invention described herein, species of Listeria were screened for utilization of a variety of carbon sources on the Biolog MT MicroPlate ™, a commercially available (Biolog, Inc., Hayward, Ca.) 96-well microplate designed to test the ability of an inoculated microorganism suspension to utilize a panel of different carbon sources. Each well of the panel contains a tetrazolium redox dye and a buffered nutrient medium. A panel of carbon sources of the present invention was added to the MT plates and dried before inoculating with a microorganism suspension. Approximately 0.6 mg of each carbon source (e.g., 15 $\mu l$ of a 4% stock solution) was added to each well. The Biolog MT MicroPlate ™ was arranged so that there was one control well with no carbon source and the remaining wells contained individual carbon sources or a mixture of carbon sources. The indicator plate was then incubated at an appropriate temperature of 37° C. for 24 hours. Many of the carbon source reactions were apparent even by 1 hour. The results are shown in Table 2.

TABLE 2

DIFFERENTIAL METABOLISM OF LISTERIA SPECIES AS MEASURED BY REDOX DYE REDUCTION ON A MICROPLATE ™ TEST PANEL

| Species | D-Glu L-Mal Mtl | 5'AMP | Gly β-Met. | D-Xyl | L-Rha | Xylit | Suc | α-D-Lac | L-Lct | F6P G6P G1P | Gen. Path. |
|---|---|---|---|---|---|---|---|---|---|---|---|
| L. monocytogenes | 0 | 100 | 100 | 78[a] | 89[a] | 100 | 22 | 78[a] | 67 | 56 | + |
| L. ivanovii | 0 | 100 | 100[a] | 100[a] | 0 | 0 | 0 | 100[a] | 100 | 100 | + |

TABLE 2-continued

DIFFERENTIAL METABOLISM OF LISTERIA SPECIES AS MEASURED BY REDOX DYE REDUCTION ON A MICROPLATE ™ TEST PANEL

| Species | D-Glu L-Mal Mtl | 5'AMP | Gly β-Met. | D-Xyl | L-Rha | Xylit | Suc | α-D-Lac | L-Lct | F6P G6P G1P | Gen. Path. |
|---|---|---|---|---|---|---|---|---|---|---|---|
| L. innocua | 0 | 100 | 100 | 100$^a$ | 100$^a$ | 100 | 50$^a$ | 100$^a$ | 0 | 0 | — |
| L. welshimeri | 0 | 100 | 100 | 100$^a$ | 50$^a$ | 100 | 50$^a$ | 100$^a$ | 0 | 0 | — |
| L. seeligeri | 0 | 100 | 100 | 100$^a$ | 0 | 100 | 0 | 100$^a$ | 0 | 0 | — |
| L. grayi | 100 | 0 | 100$^a$ | 0 | 0 | 0 | 0 | 0 | 0 | 0 | — |
| L. murrayi | 100 | 0 | 100 | 0 | 0 | 0 | 0 | 0 | 0 | 0 | — |

KEY:
D-Glu = D-gluconic acid
5'AMP = Adenosine 5'-monophosphate
L-Mal = L-malic acid
Mtl = Mannitol
Gly = Glycerol
β-Met = β-methyl glucoside
D-Xyl = D-xylose
L-Rha = L-rhamnose
Xylit = Xylitol
Suc = Sucrose
α-D-Lac = α-D-Lactose
L-Lct = L-lactic acid
F6P = fructose-6-phosphate
G6P = glucose-6-phosphate
G1P = glucose-1-phosphate
Gen. Path. = generally pathogenic
$^a$Indicates reactions that are negative or very weak after 2 hours, but positive after 24 hours.

The numbers in Table 2 indicate the percentage of strains of the particular species tested that were able to utilize the carbon source. From the data, it is evident that differences exist between the strains of a single species of Listeria.

The carbon sources L-lactic acid and hexose-phosphate (e.g., glucose-1-phosphate (G1P)) are of particular interest in this regard; these carbon sources are utilized by some but not all of the strains currently regarded as L. monocytogenes and by most if not all strains of L. ivanovii. Since the overwhelming number of listeriosis cases involve these species, the ability to distinguish strains of L. monocytogenes and L. ivanovii offers the important potential to distinguish the pathogenic strains from the non-pathogenic strains.

In this regard, both L-lactic acid and hexose-phosphates are expected to be present in relatively high levels inside the human body and if they can be utilized by the Listeria it would allow the Listeria to grow more easily in vivo. It has been recently shown that utilization of L-lactic acid by N. gonorrhoeae, in competition with leukocytes, gives it an advantage in escaping the normal defense processes of the human immune system. B. E. Britigan et al., J. Clin. Invest., 81:318 (1988). D. J. Hassett and M. S. Cohen, FASEB J., 3:2574 (1989).

While there has heretofore been no suggestion that utilization of hexose phosphates is involved in pathogenicity, Listeria does grow as an intracellular pathogen and glucose (and other hexoses) are phosphorylated when transported into the cell. Therefore, the level of hexose phosphate should exceed the level of free hexose and provide a growth advantage to any invading bacteria capable of utilizing hexose phosphate as a carbon source.

Other links have been found between utilization of specific carbon source and pathogenicity of a certain species. This literature was discussed in a review by H. Smith, J. Gert. Microbiol., 136:377 (1990). For example, Corynebacterium renale and Proteus mirabills can grow in the kidneys and cause severe damage due, at least in part, to their synthesis of a urease enzyme which allows them to utilize urea. Another example is Brucella abortus, an etiologic agent of brucellosis, a disease which results in fetal abortions in many animal species. Fetal tissues contain high levels of erythritol, and this bacterium is rather unusual in having the capability to utilize erythritol as a carbon source.

EXAMPLE TWO

Strain Differentiation

Using the invention described herein, strains of species of Listeria were screened for growth on a variety of carbon sources on the Biolog MT MicroPlate ™, a commercially available (Biolog, Inc., Hayward, Ca.), as described in Example One. The results are shown in Table 3. The listed species designations are those on the strain upon its receipt. The abbreviations used in Table 3 are as follows: + =positive reaction; +$^a$=negative or very weak reaction after 2 hours; − −=negative reaction; D-Glu=D-gluconic acid; L-Mal=L-malic acid; Mtl=mannitol; 5'AMP=adenosine 5'-monophosphate; Gly=glycerol; β-Met.=β-methyl glucoside; L-Rha=L-rhamnose; D-Xyl=D-xylose; Xylit.=xylitol; L-Lct=L-lactic acid; F6P=fructose-6-phosphate; G6P=glucose-6-phosphate; G1P=glucose-1-phosphate; Suc=sucrose; α-D-Lac=α-D-lactose.

It is clear from Table 3 that the method of the present invention is able to differentiate between strains of particular Listeria species. The source of the strains is indicated in Table 4.

TABLE 3

REACTIONS OF STRAINS OF LISTERIA SPECIES IN BIOLOG'S TEST PANEL

| Species | Strain | D-Glu L-Mal Mtl | 5'Amp | Gly β-Met. | L-Rha | D-Xyl | Xylit. | L-Lct | F6P G6P G1P | Suc | α-D-Lac |
|---|---|---|---|---|---|---|---|---|---|---|---|
| L. monocytogenes | 1293 | − | + | + | +$^a$ | − | + | − | − | + | + |
|  | 2128 | − | + | + | − | +$^a$ | + | + | + | − | +$^a$ |
|  | 2144 | − | + | + | +$^a$ | +$^a$ | + | + | + | + | − |
|  | 2198 | − | + | + | +$^a$ | +$^a$ | + | − | +$^a$ | − | +$^a$ |
|  | 8276 | − | + | + | +$^a$ | +$^a$ | + | − | − | − | +$^a$ |
|  | 8277 | − | + | + | +$^a$ | +$^a$ | + | + | − | − | +$^a$ |
|  | 8278 | − | + | + | +$^a$ | +$^a$ | + | − | + | − | +$^a$ |
|  | 8279 | − | + | + | +$^a$ | +$^a$ | + | + | +$^a$ | − | +$^a$ |
|  | 8280 | − | + | + | +$^a$ | − | + | +$^a$ | + | − | − |
| L. ivanovii | 2103 | − | + | +$^a$ | − | +$^a$ | − | + | − | − | +$^a$ |
|  | 9076 | − | + | +$^a$ | − | +$^a$ | − | + | + | − | +$^a$ |
| L. innocua | 2102 | − | + | + | +$^a$ | +$^a$ | + | − | + | − | +$^a$ |
|  | 9075 | − | + | + | +$^a$ | +$^a$ | + | − | − | +$^a$ | +$^a$ |
| L. welshimeri | 2105 | − | + | + | +$^a$ | +$^a$ | + | − | − | − | +$^a$ |
|  | 9079 | − | + | + | − | +$^a$ | + | − | − | +$^a$ | +$^a$ |
| L. seeligeri | 2104 | − | + | + | − | +$^a$ | + | − | − | − | +$^a$ |
|  | 9078 | − | + | + | − | +$^a$ | + | − | − | − | +$^a$ |
| L. grayi | 2101 | + | − | +$^a$ | − | − | − | − | − | − | − |
|  | 9074 | + | − | +$^a$ | − | − | − | − | − | − | − |
| L. murrayi | 2199 | + | − | + | − | − | − | − | − | − | − |
|  | 9077 | + | − | + | − | − | − | − | − | − | − |

TABLE 4

CHARACTERIZATION OF STRAINS OF SPECIES OF LISTERIA

| STRAIN # | SPECIES | SOURCE | SOURCE # |
|---|---|---|---|
| 2101 | L. grayi | CCUG | EF-4983 |
| 9074$^T$ | L. grayi | ATCC | 19120 |
| 2086 | L. innocua | FDA | 2411KA |
| 2283 | L. innocua | FSIS | 20C-26 |
| 2323 | L. innocua | NVSL | 89-357 |
| 2720 | L. innocua | NVSL | 88-61- |
| 2729 | L. innocua | NVSL | 87-481 |
| 2775 | L. innocua | FDA/Sea. | Sea3552 |
| 2949 | L. innocua | CSDHS | 894345-7 |
| 3067 | L. innocua | FDA/Minn. | 12 |
| 2102 | L. innocua | FDA/Minn. | L-0705 |
| 9075$^T$ | L. innocua | ATCC | 33090 |
| 2103 | L. ivanovii | FDA/Minn. | KC-1714 |
| 9076$^T$ | L. ivanovii | ATCC | 19119 |
| 1293 | L. monocytogenes | Carey |  |
| 2128$^T$ | L. monocytogenes | ATCC | 15313 |
| 2144 | L. monocytogenes | U of IL |  |
| 2198 | L. monocytogenes | CCUG | 1452 |
| 8276 | L. monocytogenes | Iowa State | VM-4 |
| 8277 | L. monocytogenes | CCUG | EF-440 |
| 8278 | L. monocytogenes | CCUG | EF-441 |
| 8279 | L. monocytogenes | CCUG | EF-442 |
| 8280 | L. monocytogenes | CCUG | EF-444 |
| 2199 | L. murrayi | CCUG | EF-4984 |
| 9077$^T$ | L. murrayi | ATCC | 25401 |
| 2104 | L. seeligeri | FDA/Minn. | CA-0705 |
| 9078$^T$ | L. seeligera | ATCC | 35967 |
| 2105 | L. welshimeri | FDA/Minn. | CU-0705 |
| 9079$^T$ | L. welshimeri | ATCC | 35897 |

*The legend for Table 4 is shown on the following page.

Legend for Table 4:
ATCC = American Type Culture Collection (type strains)
CCUG = Culture Collection University of Gothenburg, Sweden
FDA/Minn. = Food & Drug Administration Lab, Minneapolis, MN
FDA/Sea = FDA Seattle
FSIS = Food Safety and Inspection Service
IOWA ST. = Iowa State University, Paul Hartman
CAREY = Roberta Carey, St. Francis Hospital, Evanston, IL
U of IL = University of Illinois, Chicago Medical Center
NVSL = National Veterinary Services Laboratory, Ames, IA
CSDHS = California State Department of Health Services
$^T$ = Indicates type strain.

EXAMPLE THREE

Utilization of Tagatose Using the invention described herein, species of Listeria were screened for utilization of tagatose on the Biolog MT MicroPlate ™, a commercially available (Biolog, Inc., Hayward, Ca.), as described in the previous examples (One through Four). Approximately 0.6 mg (e.g., 15 μl of a 4% stock solution) of tagatose was added to designated wells of the MT plates and dried before inoculating with a microorganism suspension. The Biolog MT MicroPlate ™ was arranged so that there was one control well with no carbon source. The indicator plate was then incubated at an appropriate temperature of 37° C. for 24 hours. At four and twenty-four hours, L. welshimeri was strongly positive. None of the other strains were positive, with the very rare exception of L. monocytogenes strains which were only very weakly positive.

EXAMPLE FOUR

Detection and Species Level Identification by Differential Metabolism of Various Alanine Dipepties and α-Methyl Glucoside Using the invention described herein, species of Listeria were screened for utilization of a variety of carbon sources on the Biolog MT MicroPlate ™, a commercially available (Biolog, Inc., Hayward, Ca.), as described in Examples One and Two. The results are shown in Table 5 (DL-Ala/DL-Leu=DL-alanine and DL-leucine in combination as a cocktail); DL-Ala-Gly=DL-alanyl-glycine; L-Ala=L-alanine; L-Ala-Gly=L-alanyl-glycine; w=weak reaction; +=positive reaction; +$^s$=strong positive reaction; −=negative reaction).

TABLE 5

REACTIONS OF STRAINS OF LISTERIA SPECIES IN BIOLOG'S TEST PANEL

| Listeria Species | Strain Number | DL-Ala DL-Leu | DL-Ala-Gly | L-Ala | L-Ala-Gly | α-Methyl Glucoside |
|---|---|---|---|---|---|---|
| L. ivanovii | 9076 |  |  |  | − | − |
|  | 2103 |  |  | − | − | − |
| L. monocytogenes | 2128 | − | − | − | − | +$^s$ |
|  | 8277 | − | − | − | − | +$^s$ |
|  | 8279 |  |  |  | − | − |
| L. innocua | 9075 | − | w | w | − | w |
|  | 2102 | + | w | w | w | − |
| L. seeligeri | 9078 |  |  | − | − | + |
|  | 2104 |  |  | − | − | − |
| L. welshimeri | 9079 |  |  | − | − | − |
|  | 2105 |  |  | − | − | − |
| L. grayi | 9074 |  |  | − | − | − |
|  | 2101 |  |  | − | − | − |
| L. murrayi | 9077 |  |  | − | − | − |
|  | 2199 |  |  | − | − | − |

Based on the results in Table 5, L-alanine and L-alanine peptides appear to be useful for differentiation between L. monocytogenes and L. innocua. Due to the biochemical similarities between L. monocytogenes and L. innocua, the ability to distinguish strains of these species offers the important potential to distinguish the pathogenic strains from the non-pathogenic strains. The source of the strains is shown in Table 4.

EXAMPLE FIVE

Utilization of Alanine-Peptides By L. monocytogenes and L. innocua

Using the invention described herein, L. monocytogenes and L. innocua were tested for utilization of a variety of alanine-peptides as carbon sources on the Biolog MT MicroPlate ™, as described in the previous examples (One through Three). Approximately 0.6 mg of each carbon source (e.g., 30 μl of a 2% (20 mg/ml) stock solution) was added to each well. The alanine-peptides all contained L-amino acids and included: alanyl-alanine, alanyl-aspartic acid, alanyl-glutamic acid, alanyl-glutamine, alanyl-histidine, alanyl-isoleucine, alanyl-leucine, alanyl-lysine, alanyl-methionine, alanyl-phenylalanine, alanyl-proline, ahanyl-valine, alanyl-glycine, and alaninamide. L-alanine and α-methyl-D-glucoside were also included in this test panel. The Biolog MT MicroPlate ™ was arranged so that there was one control well with no carbon source and the remaining wells contained individual carbon sources. The indicator plate was then incubated at an appropriate temperature of 37° C. for 24 hours.

In this test panel, L. monocytogenes was only able to utilize α-methyl glucoside. In contrast, L. innocua was able to utilize alanyl-isoleucine, alanyl-leucine, alanyl-methionine, alanyl-phenylalanine, alanyl-proline, atanyl-valine, alanyl-glycine, alanyl-histidine, and alanyl-glutamine. Weak positive reactions were observed for L. innocua with alanyl-alanine, alanyl-lysine, and alanine. L. innocua was unable to utilize α-methyl glucoside, alanyl-aspartic acid or alanyl-glutamic acid.

EXAMPLE SIX

Utilization of Alanine-Peptides Comprising a Peptide Cocktail

Using the invention described herein, L. monocytogenes and L. innocua were tested for utilization of an alanine-peptide cocktail as a carbon source on the Biolog MT MicroPlate ™, as described in the previous examples (One through Three). In this panel, α-methyl glucoside was also tested. Approximately 0.6 mg of each of three carbon sources (e.g., 30 μl of a 2% (20 mg/ml) stock solution) was added to each well. The alanine-peptides all contained L-amino acids and included alanyl-alanine, alanyl-methionine, and alanyl-valine. The Biolog MT MicroPlate ™ was arranged so that there was one control well with no carbon source. The indicator plate was then incubated at an appropriate temperature of 37° C. for 24 hours.

In this test panel, L. innocua was able to utilize the alanyl-alanine, alanyl-methionine, alanyl-valine cocktail, but was unable to utilize n-methyl glucoside. L. monocytogenes was unable to utilize the peptide cocktail, but was able to utilize n-methyl glucoside. Thus, the combination of results for the peptide cocktail and α-methyl glucoside provide useful reactions in the differentiation of the metabolically similar organisms, L. monocytogenes and L. innocua.

What is claimed is:

1. A method for detecting a species of the genus Listeria comprising:
    a) exposing a sample suspected of containing microorganisms belonging to the genus Listeria to a metabolically effective amount of α-methyl glucoside capable of being metabolized by Listeria monocytogenes but not Listeria ivanovii, for a time and under conditions sufficient for said Listeria monocytogenes to metabolize said α-methyl glucoside; and
    b) detecting any metabolism of said α-methyl glucoside by said Listeria monocytogenes, thereby determining the presence of said Listeria monocytogenes.

2. The method of claim 1 further comprising, prior to said exposing step, subjecting said sample to an enrichment treatment which will enhance the population of the genus Listeria in said sample.

3. A method for detecting strains of L. welshimeri comprising:
    a) exposing a sample suspected of containing microorganisms belonging to the genus Listeria to a metabolically effective amount of tagatose capable of being metabolized by L. welshimeri but not metabolized by other species of Listeria, for a time and under conditions sufficient for metabolism by L. welshimeri; and
    b) detecting metabolism of said tagatose by measuring oxidative respiration, thereby determining the presence of L. welshimeri.

4. The method of claim 3 further comprising, prior to said exposing step, subjecting said sample to an enrichment treatment which will enhance the population of the genus Listeria in said sample.

5. A method for distinguishing between the species *L. innocua* and *L. monocytogenes* comprising:

a) exposing a sample suspected of containing said microorganisms *L. innocua* and *L. monocytogenes* to a metabolically effective amount of one or more carbon sources capable of being metabolized by *L. innocua* but not metabolized by *L. monocytogenes* for a time and under conditions sufficient for said *L. innocua* to metabolize said one or more carbon sources, wherein said one or more carbon sources is selected from the group consisting of L-alanine, L-alanyl glycine, L-alanyl-alanine, L-alanyl-glutamine, L-alanyl-histidine, L-alanyl isoleucine, L-alanyl leucine, L-alanyl-methionine, L-alanyl-phenylalanine, L-alanyl-proline, L-alanyl valine, and a cocktail consisting of L-alanyl-alanine, L-alanyl-methionine, and L-alanyl valine; and b) detecting any metabolism of said one or more carbon sources thereby determining the presence of *L. innocua*.

6. The method of claim 5 further comprising, prior to said exposing step, subjecting said sample to an enrichment treatment which will enhance the population of the genus Listeria in said sample.

* * * * *